United States Patent [19]

Huene

[11] Patent Number: 5,314,484
[45] Date of Patent: May 24, 1994

[54] BI-AXIAL ELBOW JOINT REPLACEMENT

[76] Inventor: Donald R. Huene, 201 N. Valeria St., Fresno, Calif. 93701

[21] Appl. No.: 6,126

[22] Filed: Jan. 19, 1993

Related U.S. Application Data

[63] Continuation of Ser. No. 740,918, Aug. 6, 1991, abandoned.

[51] Int. Cl.$^5$ .................................................. A61F 2/38
[52] U.S. Cl. ............................................ 623/20; 623/18
[58] Field of Search ............................. 623/18, 19, 20, 21

[56] References Cited

U.S. PATENT DOCUMENTS

| | | | |
|---|---|---|---|
| 3,638,243 | 2/1972 | Campbell, Jr. et al. . | |
| 3,708,805 | 1/1973 | Scales et al. .................... | 3/1 |
| 3,765,033 | 10/1973 | Goldberg et al. ............. | 3/1 |
| 3,772,709 | 11/1973 | Swanson ........................ | 623/20 |
| 3,816,854 | 6/1974 | Schlein . | |
| 3,824,630 | 7/1974 | Johnston ....................... | 623/20 |
| 3,852,831 | 12/1974 | Dee . | |
| 3,863,274 | 2/1975 | Glabiszewski . | |
| 3,868,730 | 3/1975 | Kaufer et al. . | |
| 3,909,854 | 10/1975 | Martinez ....................... | 3/1.911 |
| 3,990,117 | 11/1976 | Pritchard et al. . | |
| 4,038,704 | 8/1977 | Ring . | |
| 4,057,858 | 11/1977 | Helfet . | |
| 4,079,469 | 3/1978 | Wadsworth . | |
| 4,088,130 | 5/1978 | Applegate . | |
| 4,129,902 | 12/1978 | Harmon . | |
| 4,131,956 | 1/1979 | Treace . | |
| 4,224,695 | 9/1980 | Grundei et al. . | |
| 4,280,231 | 7/1981 | Swanson . | |
| 4,293,963 | 10/1981 | Gold et al. . | |
| 4,378,607 | 4/1983 | Wadsworth . | |
| 4,383,337 | 5/1983 | Volz et al. . | |
| 4,520,802 | 6/1985 | Mercer et al. . | |
| 4,538,306 | 9/1985 | Sörre et al. ................... | 623/20 |
| 4,777,941 | 10/1988 | Borig et al. ................... | 623/27 |
| 4,802,467 | 2/1989 | Pansiera ........................ | 623/39 |
| 4,881,299 | 11/1989 | Young et al. . | |
| 4,915,098 | 4/1990 | Young et al. . | |
| 5,000,170 | 3/1991 | Young et al. ................. | 623/39 |

FOREIGN PATENT DOCUMENTS 2177603A 1/1987 United Kingdom .
2182714A 5/1987 United Kingdom .

*Primary Examiner*—Randy C. Shay
*Attorney, Agent, or Firm*—Joseph W. Berenato, III

[57] ABSTRACT

A bi-axial orthopaedic device includes a hinge block having longitudinal and transverse axes, an ulna pivot, a humerus pivot, and ulna and humerus spike mounting devices; and humerus and ulna spikes which each have a longitudinal axis, a first end portion having a pivot, a second end portion adapted to be inserted in an ulna or humerus. The ulna spike first end portion is pivotally mounted in the ulna spike mounting device and the humerus spike first end is pivotally mounted in the humerus spike mounting device. Each spike mounting device includes mechanisms for permitting the respective spike to pivot substantially through 90°. The spikes have a first extended position relative to the hinge block and each other where their longitudinal axes are offset from one another and substantially extend in the direction of the longitudinal axis of the hinge block, and a second folded position where their longitudinal axes are substantially parallel to each other and transverse to the longitudinal axis of the hinge block. In the folded position, the second ends portions of the spikes extend in the same direction; and the second ends extend in an opposite direction when in the extended position. Further, the humerus and ulna spike second ends include surfaces for providing orthopaedic support thereon.

20 Claims, 3 Drawing Sheets

FIG. 1
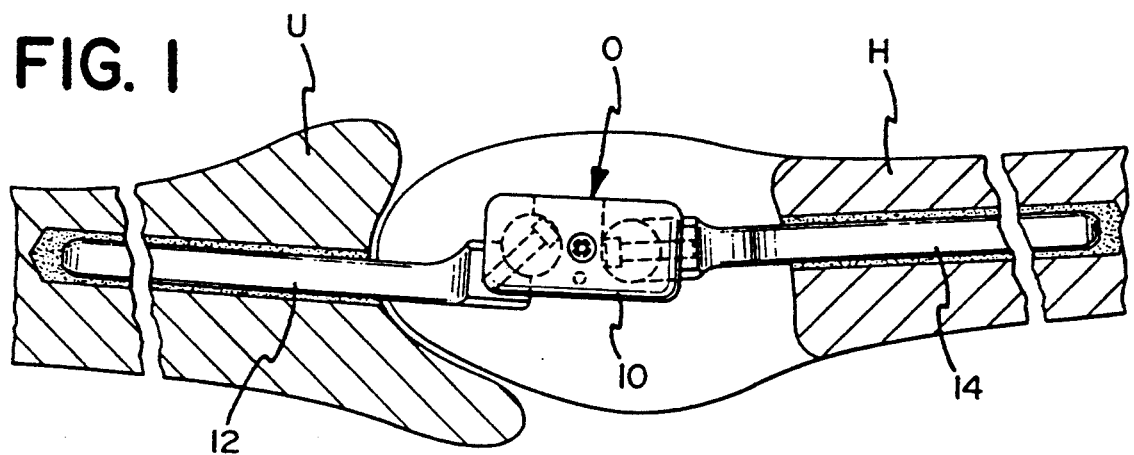
FIG. 2
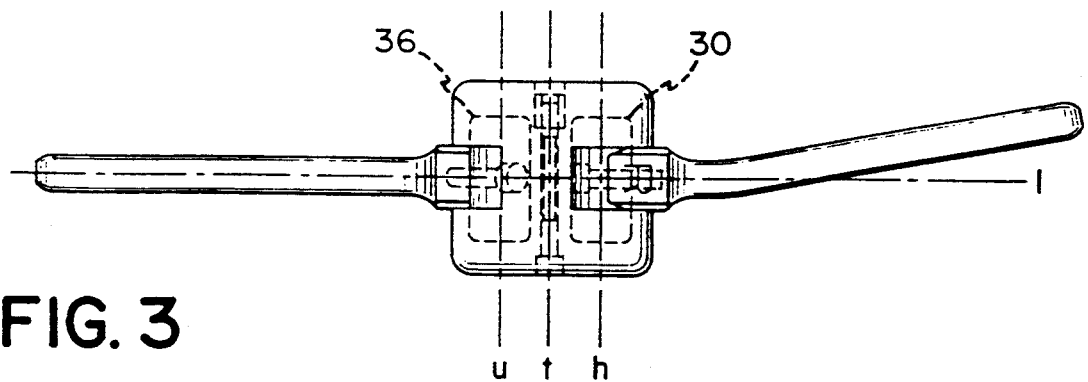
FIG. 3
FIG. 4
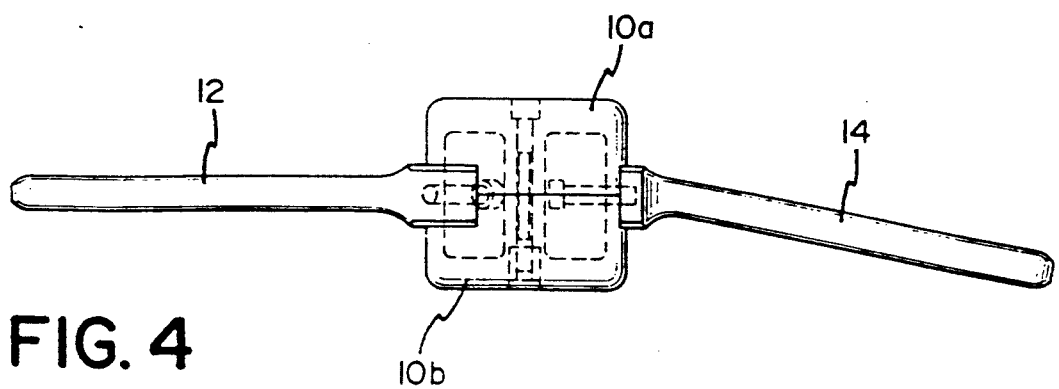

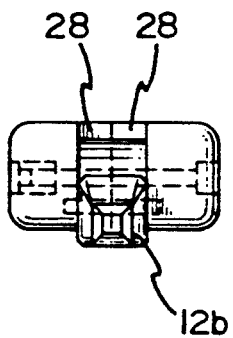
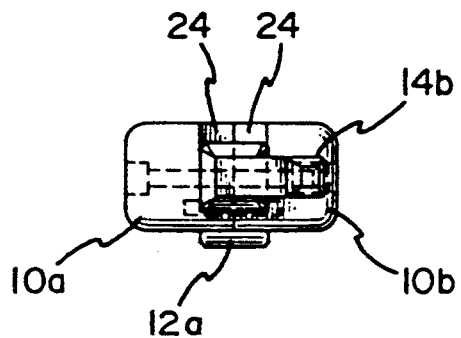
FIG. 5  FIG. 6
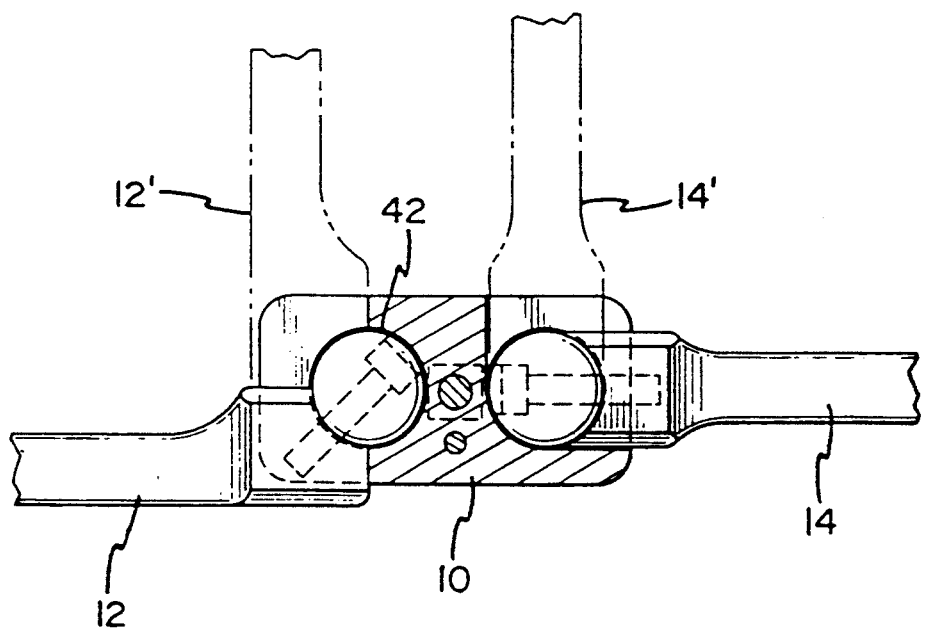
FIG. 7

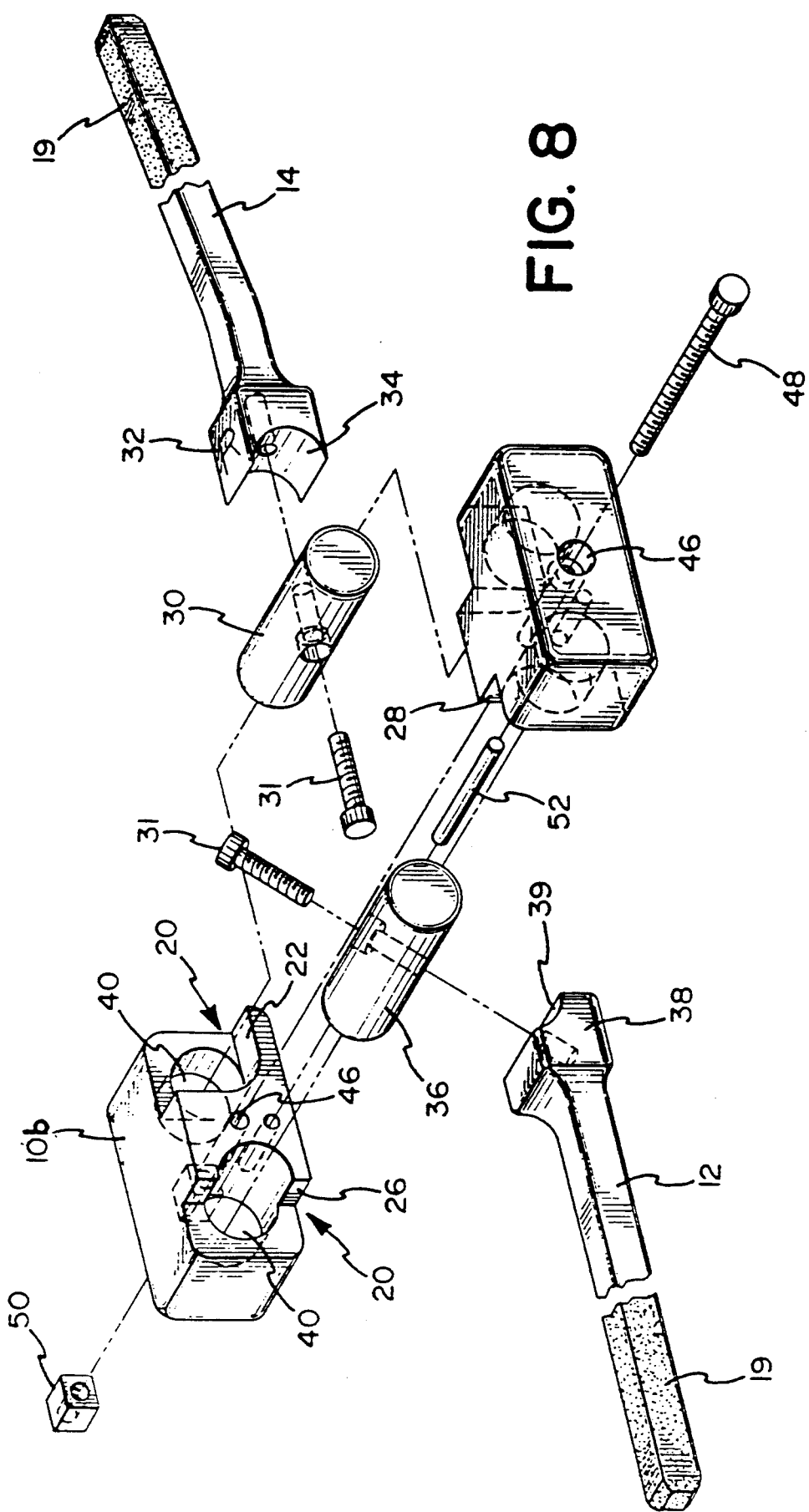

BI-AXIAL ELBOW JOINT REPLACEMENT

This is a continuation of copending application Ser. No. 07/740,918 filed on Aug. 6, 1991, now abandoned.

FIELD OF THE INVENTION

The present invention relates generally to a bi-axial orthopaedic device and in particular, to a bi-pivotal elbow replacement which minimizes stress placed on the humerus and ulna from the medullary spikes of the orthopaedic device.

BACKGROUND OF THE INVENTION

Elbow prostheses are generally totally restrained (hinged), a semi-restrained, or unrestrained (hingeless). The amount of damage to the natural joint which is desired to be replaced determines the type of elbow prosthesis to be implanted in place of the diseased or damaged natural joint. Unrestrained (hingeless) prostheses are available which provide good joint stability with minimum bone removal while providing normal flexion and extension motion as there is no built-in constraint producing strain on the seating of the prosthesis. However, such minimally constrained surface replacement elbows can only be used when the bone shaft is still strong and its soft tissue/ligaments are functional as these prostheses rely on the elbow's ligamentous structure to maintain joint stability.

Unfortunately, most elbows that require replacement have ligamentous laxity or instability and/or inadequate bone stock which consequently requires use of the "constrained type" of elbow prosthesis. Orthopaedic devices of the constrained or semi-constrained type employ two arms or spikes which are inserted in the medullary canals of the humerus and the ulna, and are rotatably interconnected via a hinge to provide stability. While total elbow prostheses are known which have a semi-constrained interface at the humeralulnar joint, the arms or spikes of these devices very often cause erosion of the humerus and ulna bones due to the inability of the prostheses to dissipate significant joint stresses. For example, when an elbow is subjected to forceful extension, such as may occur when throwing a baseball, presently available prostheses do not provide the damping or shock absorbing action usually provided by the natural soft tissues of the elbow.

Furthermore, the hinged joint of known prostheses actually enables the shock to travel through both spikes of the prosthetic device, placing stress on the bones in which the spikes are inserted. The jolts and forces associated with this stress gradually chip away at the bone and, after a period of time, the spikes' adhesive contact with the medullary canal of the bones is loosened. Consequently, after a year or two, replacement of these prostheses is necessary. Moreover, the deterioration of the bone canal or shaft may make subsequent replacements of the joint more difficult or impossible.

Orthopaedic devices for use in total elbow replacement which address the need for normal flexion and extension motion and joint stability are represented by U.S. Pat. Nos. 3,816,854; 4,079,469; 4,224,695; and 4,383,337. All of these prostheses employ the single pivot hinge arrangement as discussed above.

U.S. Pat. No. 4,777,941 to Borig et al. discloses an orthopaedic hinge for limiting the flexion and extension of an associated body part, for example, a knee or elbow. The hinge taught by Borig et al. employs a housing and a pair of control arms which are rotatably mounted about respective pivot points in the housing. However, this bi-pivotal hinge is for use in a brace which externally supports the associated joint which may be an orthopaedic implant. The bi-pivotal arrangement minimizes bending moments created at the joint due to misalignment of the centers of the external hinge and the joint. Nowhere does Borig et al. suggest that its external bi-pivotal hinge can be used in an implant for replacing a joint or that its hinge reduces stresses which travel through the arms of an orthopaedic hinge.

In so far as applicant is aware, all prostheses for elbow replacement employ a single pivot hinge resulting in an undesirable connection between the spikes of the orthopaedic device. This humeralulnar joint connection enables stress to travel through both spikes, eventually damaging the humerus and ulna bones. According to conventional practices, constrained prostheses should have little play in order to compensate for the instability of the natural ligaments. The additional joint stability, however, increases the amount of stress which travels through the spikes and causes the deterioration of the natural bones as described above.

Thus, it can be seen that there is a need for an orthopaedic device suitable for a total elbow replacement which provides the necessary constraint for joint stability but which has spikes which are not interconnected and thus tightly affixed together. Accordingly, the transfer of strain or deformation to the medullary canals of the bones is prevented, as is the resultant deterioration of the humerus and ulna.

OBJECTS AND SUMMARY OF THE INVENTION

It is an object of the present invention to provide a bi-axial orthopaedic device which decreases the amount of stress transferred between the spikes of the device due to natural joint movements. Thus, it is a feature of the invention to release strain applied to the medullary canals of the bones which causes deterioration.

It is another object of the invention to provide a bi-axial orthopaedic device which lasts longer than conventional elbow prostheses to reduce the number of replacements of the orthopaedic joint implant.

It is a further object of the present invention to provide an orthopaedic device with a pair of spikes that are longer than conventional spikes to minimize the possibility of the spikes becoming loose from the bones they support. In one embodiment, a ulna spike may be almost as long as the humerus spike, but perhaps ten (10) to twenty (20) percent shorter.

It is yet another object of the present invention to provide a bi-axial orthopaedic device which is simple to manufacture and to implant in a total elbow replacement operation.

A further object is to provide such an orthopaedic device which can be disassembled easily so that the hinge portion of the device can be replaced without removing the orthopaedic spikes from the bones in which they are inserted.

Another object of the present invention is to provide an orthopaedic joint replacement device which allows a natural rotation motion to be assumed, but limits the lateral motion of the joint. As a result, unnatural lateral stresses are prevented.

These and other objects are accomplished by the bi-axial orthopaedic device according to the present invention which includes a hinge block having longitudinal and transverse axes, an ulna pivot, a humerus pivot, and spike mounting means; and humerus and ulna spikes having first end portions pivotally mounted in the spike mounting means about their respective pivots and second end portions having means for insertion into a humerus and ulna to provide orthopaedic support thereon. According to the invention, the spikes are mounted to pivot substantially through 90° and have two extreme positions relative to the hinge block and each other. In a first extended position, the longitudinal axes of the spikes are off-set from one another and substantially extend in the direction of the longitudinal axis of the hinge block. In the second extreme or folded position the longitudinal axes of the spikes are substantially parallel to each other and transverse to the longitudinal axis of the hinge block.

An important feature of the bi-axial orthopaedic device according to the invention is that the hinge block includes recess means for rotatably mounting pivot pins attached to the first ends of the spikes within the hinge block. Thus, the force bearing ends of the spike are received within the hinge block so that unnatural lateral movement is prevented.

It is still another feature that the recess means have cylindrical cavities in which ends of the pivot pins are received and the diameters of the cavities provide sufficient clearance between the cavities and pivot pins to enable unrestricted rotational movement of the pivot pins. According to the present invention, the clearance between the cavity walls and mounted pivot pins provides some play to absorb the shock or forces applied to the orthopaedic spikes, thus damping shock before it is transferred to the other spike.

Another feature of the present invention is that the longitudinal axis of the humerus spike is at an angle of approximately 10°0 relative to a line perpendicular to the axis of the pivot pin so as to correspond to the natural carrying angle of an arm.

It is a further feature of the present invention to provide a humerus spike that is interchangeable within the hinge block and enables an elbow replacement for both left and right arms by simply reversing the humerus spike. Thus, it is unnecessary to provide two different prostheses, one for the left arm and one for the right arm.

Yet another feature of the invention is to provide a bi-axial orthopaedic device where fasteners connecting the spikes to their respective pivot pins are readily accessible so that replacement of the pivot pins can be done easily and without damaging the spikes firm insertion within the bones. Moreover, the fasteners (screws) do not protrude from the pivot pin surface to avoid friction with and tearing of natural joint tissues and ligaments.

BRIEF DESCRIPTION OF THE DRAWINGS

Other objects, features and advantages of the invention, and a better understanding of its construction and operation will become apparent from the following description, taken in conjunction with the accompanying drawings, in which:

FIG. 1 is a fragmentary cross-sectional view of an ulna and a humerus showing the bi-axial orthopaedic device according to the invention in an extended position;

FIG. 2 is a left side elevational view of the orthopaedic device of the present invention with certain portions of the device being shown in hidden lines;

FIG. 3 is a top plan view of the orthopaedic device of FIG. 2 showing the angular slant of the humerus spike for a left elbow replacement;

FIG. 4 is a bottom plan view of the bi-axial orthopaedic device shown in FIG. 3 which, in effect, shows the angular slant of a humerus spike for a right elbow replacement;

FIG. 5 is a rear elevational view of the bi-axial orthopaedic device of FIG. 2 looking at an end of the ulna spike.

FIG. 6 is a front elevational view of the bi-axial orthopaedic device of FIG. 2 looking at an end of the humerus spike.

FIG. 7 is an enlarged fragmentary elevational view of the bi-axial device of FIG. 2 with portions shown in cross-section.

FIG. 8 is an enlarged exploded perspective view of the orthopaedic device according to the invention.

DESCRIPTION OF THE PREFERRED EMBODIMENT

The bi-axial orthopaedic device O of the present invention (see, in general, FIG. 1) is for being implanted in a human elbow to replace the articulating surfaces of the human elbow joint. Bi-axial orthopaedic device O includes a hinge block 10 and ulna and humerus spike components 12, 14 to be respectively inserted within an ulna U an a humerus H, as shown generally in FIG. 1.

Each spike component 12, 14, which preferably have a rectangular configuration to prevent lateral rotation, has a first end 12a, 14a which serves as a pivot and is received in a respective ulna and humerus spike mounting means 16, 18 of hinge block 10, as best shown in FIG. 2. The second ends 12b, 14b of ulna and humerus spike components 12, 14 include surfaces adapted for securing the spike components within an ulna and humerus, respectively, connected to the elbow joint to be replaced. For example, the spikes may have abraded surfaces 19, as best shown in FIG. 8, for enhancing cement contact with the humerus and ulna.

As shown in FIG. 3, hinge block 10 has a longitudinal axis 1 and a transverse axis t which are perpendicular to one another. In addition, an ulna pivot axis u and a humerus pivot axis h, offset from one another and substantially parallel to the transverse axis t, extend through spike mounting means 16, 18. First ends 12a and 14a of spike components 12, 14 are designed so that they are rotatable in the respective spike mounting means 16, 18 about the ulna and humerus pivot axes u, h.

Spike mounting means 16, 18 includes means for permitting the respective spike components to pivot substantially through 90°. The configuration of spike components 12, 14 relative to hinge block 10 when an arm in which orthopaedic device 0 is implanted is in full extension is shown in FIGS. 2-4 and by the solid lines of FIG. 7. In this first extreme or extended position, spike components 12, 14 form an angle of approximately 180° as their first ends 12b, 14b extend in the direction of the longitudinal axis 1 of hinge block 10. Preferably, spike component 12 lies on a plane lower than the plane which spike component 14 lies. Spike components 12, 14 can be rotated through a 90° pivot to their second extreme or folded position. The longitudinal axes of spike components 12, 14 are substantially parallel to each other and transverse to the longitudinal axis of hinge block 10 when in this second extreme position.

The phantom lines of FIG. 7 show spike components 12' and 14' in this second folded position.

As can be seen from FIGS. 3 and 4, a preferred shape of humerus spike component 14 is such that its second end 14b extends from first end 14a at an angle. Thus, the longitudinal axis of humerus spike 14 is set at an angle to the longitudinal axis 1 of hinge block 10 when mounted in spike mounting means 18. The preferred angle would be approximately 10° to the longitudinal axis of hinge block 10 when humerus spike component 14 is in the first extended position. The appropriate angle at which the humerus spike component 14 is set should correspond to the natural carrying angle of a patient's arm.

Further, humerus spike component 14 preferably should be shaped so that its first end portion 14a reversibly interfits within spike mounting means 18. Such a reversal would change the slant of the humerus spike component 14 so that it would correspond to the natural carrying position for a right arm, rather than a left arm as shown in FIG. 3. Accordingly, this feature enables elbow replacement in both left and right arms without requiring additional spike components or hinge blocks.

Hinge block 10 may include first and second block sections 10a, 10b with inner and outer sides substantially parallel to longitudinal axis 1 of hinge block 10 when assembled together. In the inner side surfaces of block sections 10a, 10b, spike mounting means 16, 18 are disposed. Spike components 12, 14 preferably are mounted in cut-outs 20 formed on respective sides of transverse axis t of hinge block 10 as shown in FIGS. 3–4 and 8. The cut-outs 20 of first and second block sections 10a, 10b act together to pivotally support their respective spike components.

FIG. 8 illustrates an exploded view of orthopaedic device O showing the cut-outs or recesses 20 of hinge block section 10b in detail. According to a preferred embodiment of the invention, cut-outs or recesses 20 are shaped for receiving and for permitting a respective spike component of the orthopaedic device to pivot substantially through 90°. Further, cut-outs 20 of hinge block section 10a are substantially mirror images of the cut-outs of hinge block section 10b.

In order to limit pivotal movement of spike components 12, 14, cut-outs or recesses 20 include stop means 22, 24, 26 and 28. The preferred stop means, for an elbow joint, should limit the travel of each mounted spike component to a 90° pivot. These stop means 22, 24, 26 and may be in the form of walls delimiting surfaces of cut-outs 20 which preferably correspond to recessed surfaces formed in the sides of hinge block 10. Thus, the spike mounting means and stop means could be an integral part of hinge block 10 and the hinge block sections 10a and 10b of one-piece construction.

In such an embodiment, the stop means of humerus spike mounting means 18 may include a first abutment 22 spaced from and substantially parallel to the bottom of hinge block 10, and a second abutment 24 substantially perpendicular to first abutment 22. The stop means for ulna spike mounting means 16 would preferably include first and second abutments 26, 28 which are spaced from one another and disposed in a common plane. The common plane preferably is substantially perpendicular to the bottom of hinge block 10.

The sides of hinge block 10 in which ulna and humerus spike components 12, 14 are mounted are shown in FIGS. 5 and 6. The spike components 12, 14 are disposed in the extended position, and thus second abutments 24, 28 of the humerus and ulna stop means are clearly visible. The hidden lines of these figures also show means for securing the two pieces of hinge block 10 together and a stabilizing pin useful for holding the first and second sections of hinge block 10 together.

The side view of FIG. 6, looking from second end 14b of spike component 14 to hinge block 10, shows the difference between the ulna and humerus stop means. In the extended position, the first end 14a of humerus spike component 14 rests on top of first abutment 22 and a bottom portion of ulna spike first end 12b extends below the bottom of hinge block 10. Accordingly, the shape of cut-outs 20 forms the offset relationship of the spike components. The angled shape of humerus spike 14 which extends on a plane higher than that of ulna spike component 12 is also illustrated by this side view.

A humerus pivot pin 30 is preferably attached to first end 14b of humerus spike component 14 for rotation within mounting means 18, as best shown in FIGS. 2 and 8. In the extended position, first end 14a of humerus spike component 14 rests against abutment 22 of spike mounting means 18. Humerus pivot pin 30 is transversely mounted via a fastener 31 to first end 14a so as to centrally align the axis of humerus spike component 14 with the longitudinal axis 1 of hinge block 10. First end 14a has a head portion 32 extending therefrom and including a top surface 34 in which humerus pivot pin 30 is received. Head portion 32 has a longitudinal axis generally, co-axially aligned with the longitudinal axis 1 of humerus spike component 14. The top surface 34 of head portion 32 is generally concave and shaped to mate with the exterior of humerus pivot pin 30.

Likewise, an ulna pivot pin 36 is connected via a fastener 31 to the first end 12a of ulna spike component 12. The first end of ulna spike component 12 has a head portion 38 extending therefrom and including a top surface 39 upon which the ulna pivot pin 36 is mounted. Ulna pivot pin 36 is disposed on the top surface 39 so that a side surface of head portion 38 can abut abutment 26 in the extended position. Head portion 38 has a longitudinal axis generally co-axially aligned with the longitudinal axis of ulna spike component 12. The top surface 39 of head portion 38 is concave for mounting with ulna pivot pin 36.

Fastener 31 may be a threaded screw which can be threaded into a bore centrally located in pivot pins 30, 36 and their respective a head portions 32, 38. The bore of humerus head portion 32 is coaxially disposed therein in order to centrally mount humerus pivot pin 30 within the top surface of head portion 32. In a similar manner, fastening means can be used to connect ulna spike component 12 with ulna pivot pin 36. However, fastener 31 extends through ulna pivot pin 36 into a bore of ulna head portion 38 at an approximate 45° angle. Fasteners 31 are flush with pivot pins 30, 36 when securing the pivot pins to a spike component first end.

Cut-outs 20 further include cylindrical cavities 40 for receiving ends of pivot pins 30, 36 to limit an unnatural lateral side motion within the joint. These cylindrical cavities are formed beside the abutments of the stop means within hinge block sections 10a, 10b and have a diameter which provides sufficient clearance between their sidewalls and the respective pivot pins 30, 36 to enable unrestricted rotational movement of the pivot pins. As can be seen from FIG. 7, pivot pins 30, 36 are received within spike mounting means 16, 18 so that a space 42 exists therebetween. This space provides play which enables spike components 12, 14 to move within the mounting means, and thus absorbs shock.

Cylindrical cavities 40 provided in hinge block sections 10a, 10b can be spaced a selective distance apart in order to accommodate different sizes of humerus and ulna. That is, the length and width of the hinge block 10 is determined based upon the human elbow joint that is to be replaced. Accordingly, it is possible to replace hinge block 10 with a different size hinge block, without removing spike components 12, 14, if the recipient grows or requires a wider space between pivoting means of the spike components. Since the comfort and particular size of the orthopaedic device can only be determined after the implant is in position, this replaceable hinge provides an important advantage over known prior art orthopaedic devices.

Hinge block sections 10a and 10b are joined together along the longitudinal axis 1 of hinge block 10 via a fastener such as a threaded screw. As shown in FIG. 8, each hinge block section includes a threaded bore 46 for receiving a threaded screw 48 therethrough. The head of threaded screw 48 is secured flush with the outer surface of hinge block 10a and a nut 50 sits flush with the outer surface of 10b. The nut provides the locking means necessary for securely holding the block sections together.

In addition, at least one stabilizing pin 52 can extend through hinge block sections 10a and 10b in a generally transverse direction, but off center from the threaded bore 46 which receives the threaded screw 48 and locking nut 50.

In a preferred embodiment, the humerus spike component 14 has a length of about ½ to about ⅔ the length of the actual humerus attached to the replaced elbow joint; and the ulna spike component 12 has a length between about ½ to about ⅔ the length of the ulna attached to the replaced elbowing joint. Accordingly, the orthopaedic device O, according to the invention, preferably would have spike components of about equal length. Thus, a preferred orthopedic device would have a humerus spike component 14 which would extend almost up to a patient's shoulder and an ulna spike component would extend almost down to the patient's wrist. Consequently, the ulna spike component 12 according to the invention is relatively longer than those used in the prior art.

The preferred length ratio of the humerus spike component to the ulna spike component would be such that the ulna spike component would be approximately 10 to 20 percent shorter than the humerus spike component. With longer spikes than currently available for such orthopaedic devices, the elbow replacement should have less of a chance of loosening from the bones.

Hinge block 10 is preferably made of a plastic material such as polyethylene and is finished so that its exterior edge surfaces are smooth. This prevents frictional wear between the hinge block 10 and the natural ligaments remaining in the replaced elbow joint.

Additionally, the spike components can be made from a material selected from the group consisting of steel alloys, aluminum alloys, titanium alloys, plastics and composites. Thus, the orthopaedic device of the present invention is made of material that is compatible with human tissue so that infection and other deterioration is prevented in the remaining natural joint components.

While this invention has been described as having a preferred design, it is understood that it is capable of further modifications, uses and/or adaptations of the invention following in general the principle of the invention and including such departures from the present disclosure as come within the known or customary practice in the art to which to invention pertains and as may be applied to the central features hereinbefore set forth, and fall within the scope of the invention and of the limits of the appended claims.

What is claimed is:

1. An implantable artificial elbow, comprising:
   a) a hinge block having first and second spaced ends and a longitudinal axis extending therebetween;
   b) first and second pins, each pin secured to one of said ends and said pins defining parallel axes extending generally transverse to said longitudinal axis and therewith defining a plane;
   c) an ulna spike member pivotal relative to said block and including a first portion operably secured to said first pin and a second portion extending therefrom parallel to and spaced from said plane when in a first orientation;
   d) a humerus spike member pivotal relative to said block and including a first portion operably secured to said second pin and a second portion extending therefrom on said plane when in a first orientation;
   e) each of said ends includes a first face engageable with the associated member for providing said first stop so that said members may be pivoted between a first orientation in which said members engage the associated first end face and extend respectively parallel to and along said plane and a second orientation in which each said member extends at an angle relative to said longitudinal axis; and
   f) each said member second portion adapted for being secured within a respective one of an ulna and a humerus.

2. The elbow of claim 1, wherein:
   a) one of said members extends along said longitudinal axis, and the other of said members is angularly disposed relative to said longitudinal axis.

3. The elbow of claim 2, wherein
   a) said ulna member extends along said longitudinal axis.

4. The elbow of claim 2, wherein:
   a) at least one of said first faces extends perpendicularly to said plane.

5. The elbow of claim 4, wherein:
   a) each of said ends has a second face engageable with the associated member for providing a second stop so that said second orientation is no more than perpendicular to said longitudinal axis.

6. The elbow of claim 5, wherein:
   a) at least one of said second faces extends perpendicularly relative to the associated first end face.

7. The elbow of claim 1, wherein:
   a) each of said pins is pivotal, and each of said members pivots with the associated pin.

8. The elbow of claim 7, wherein:
   a) a fastener operably secures each of said members to the associated pin.

9. The elbow of claim 1, wherein:
   a) said block is comprised of a polymeric material.

10. The elbow of claim 9, wherein:
    a) each of said members is comprised of metal.

11. The elbow of claim 10, wherein:
    a) each of said members is comprised of a material selected from the group consisting of steel, aluminum, titanium, and alloys thereof.

12. The elbow of claim 1, wherein:

a) each of said first portion has an element surrounding at least a portion of the associated pin.

13. The elbow of claim 12, wherein:
a) each of said elements are arcuate for mating with the associated pin.

14. The elbow of claim 1, wherein:
a) each of said second portions has a textured surface for enhancing adhesive securement of the associated member to the respective one of the ulna and humerus.

15. An implantable artificial elbow, comprising:
a) a polymeric hinge block having spaced first and second ends and a longitudinal axis extending therebetween;
b) first and second pins, each pin secured to one of said ends and said pins defining parallel axes extending generally transverse to said longitudinal axis and therewith defining a plane;
c) a metallic ulna member pivotal relative to said block and including a first portion connected to said first pin and a second portion extending therefrom parallel to and spaced from said plane when in a first orientation;
d) a metallic humerus member pivotal relative to said block and including a first portion connected to said second pin and a second portion extending on said plane when in a first orientation;
e) one of said members extends along said longitudinal axis, and the other of said members is angularly disposed relative to said longitudinal axis;
f) each of said members is pivotal between said first orientation in which the member extends parallel to or along said plane, respectively, and a second orientation angularly disposed relative to said plane; and
g) each of said second portions is adapted for being secured with a respective one of an ulna and a humerus.

16. The elbow of claim 15, wherein:
a) each of said ends includes a first face engageable with the associated member and providing a first stop positioning the associated member in said first orientation.

17. The elbow of claim 16, wherein:
a) at least one of said first faces extends transverse to said longitudinal axis.

18. The elbow of claim 17, wherein:
a) each of said ends includes a second face engageable with the associated member and providing a second stop so that said second orientation is no more than perpendicular to said longitudinal axis.

19. The elbow of claim 18, wherein:
a) at least one of said second faces extends perpendicularly relative to the associated end face.

20. The elbow of claim 15, wherein:
a) a fastener operably secures each first portion to the associated pin.

* * * * *